United States Patent [19]

Levey et al.

[11] Patent Number: 4,919,981
[45] Date of Patent: Apr. 24, 1990

[54] ARTIFICIAL HORTICULTURAL PRODUCT AIR FRESHENER

[76] Inventors: John Levey; Idelle B. Levey, both of 4059 Mariner's Cir., Westlake Village, Calif. 91361

[21] Appl. No.: 383,855

[22] Filed: Jul. 21, 1989

[51] Int. Cl.$^5$ .......................... A41G 1/00; B65D 1/04
[52] U.S. Cl. ....................................... 428/26; 239/44; 428/34.1; 428/905
[58] Field of Search .................. 428/24, 34.1, 905, 25, 428/26; 239/44, 145

[56] References Cited

U.S. PATENT DOCUMENTS

| | | | |
|---|---|---|---|
| 1,839,073 | 12/1931 | Wright | 428/905 X |
| 1,858,148 | 5/1932 | Freese | 428/24 X |
| 2,702,441 | 2/1955 | Jones | 428/24 X |
| 3,804,331 | 4/1974 | Levey | 239/60 X |
| 4,065,016 | 12/1977 | Perkins | 428/34.1 X |
| 4,346,059 | 8/1982 | Spector | 428/905 X |

FOREIGN PATENT DOCUMENTS 988670  4/1965  United Kingdom ................ 428/905

Primary Examiner—Henry F. Epstein
Attorney, Agent, or Firm—William H. Pavitt, Jr.; Ralf H. Siegemund; Daniel L. Dawes

[57] ABSTRACT

An improved artificial horticultural product air freshener comprised of a vase-like outer decorative housing formed to appear like crystal, said housing co-axially encompassing a replaceable inner aromatic fluid-containing vessel conforming generally to the shape of the inner wall of the outer housing, but spaced therefrom. The upper rim of the housing is provided with a cap through which extend, supported thereby, one or more stem-like wicks down into the bottom of the vessel and up into one or more artificial leaf-like or flower-like dispenser elements. When the fluid has been dissipated, the vessel may be replaced.

12 Claims, 3 Drawing Sheets

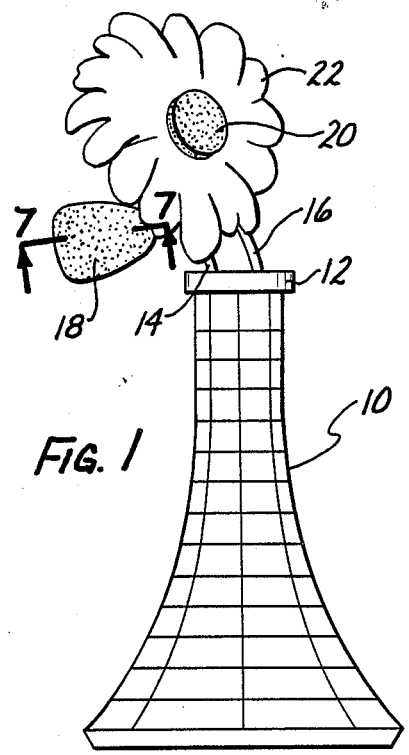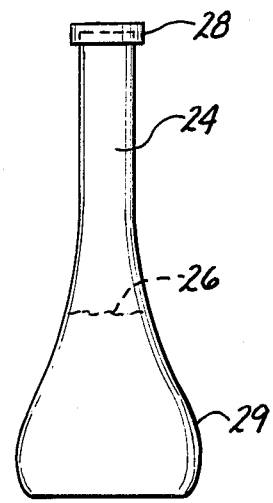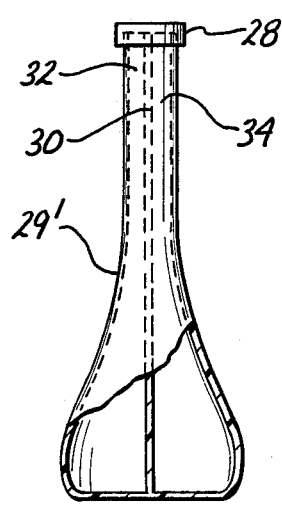
FIG. 1
FIG. 2
FIG. 3

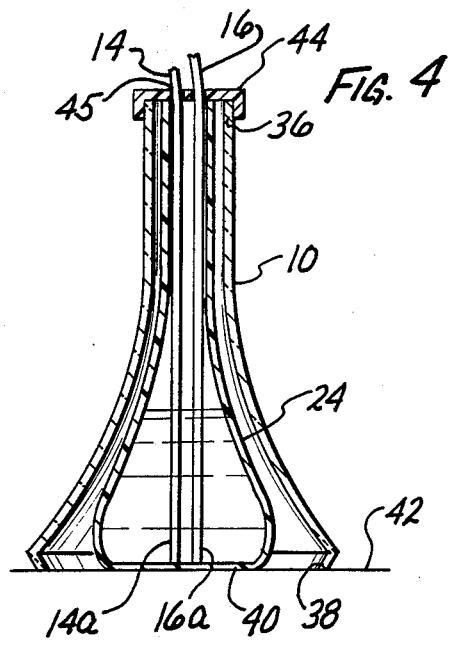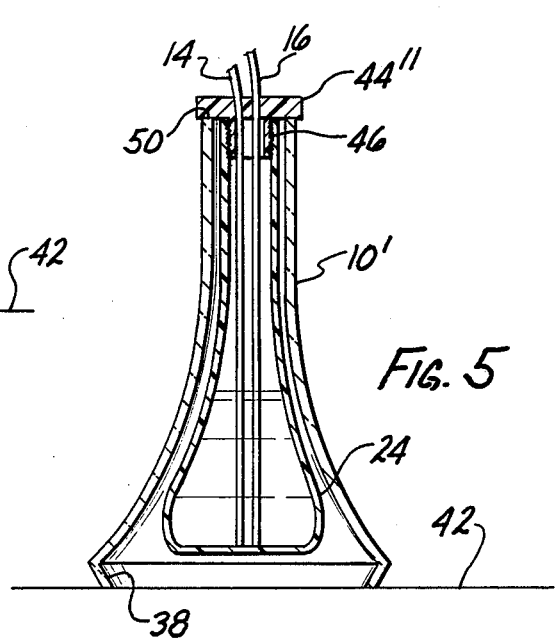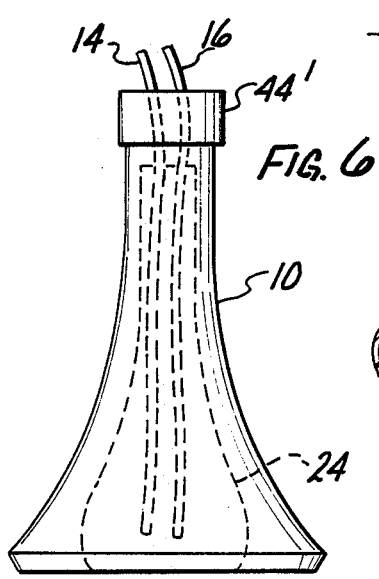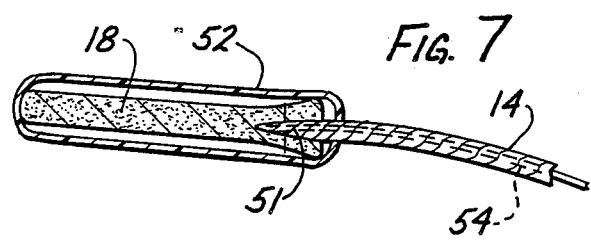

4,919,981

ARTIFICIAL HORTICULTURAL PRODUCT AIR FRESHENER

FIELD OF THE INVENTION

This invention relates to the field of air fresheners and odorizers and, particularly, such air fresheners as are decorative from the standpoint of displaying artificial flowers.

BACKGROUND OF THE INVENTION

Description of the Prior Art

Decorative air fresheners have been in use for many years. Initially, air fresheners were structured of a liquid container from which extended upwardly some type of wick which drew liquid from the container by capillary action and dissipated it into the air in the vicinity of the wick.

Commencing as far back as fifty years ago, the liquid decorative containers began to be replaced with containers of gelatinous substances which, upon exposure through some opening in the container, would exude the desired aromas or air cleansing gas. The amount of gas might be regulated by varying the size of the opening in the container. An example of such an air freshener may be seen in U.S. Pat. No. 3,804,331, issued to one of the the present inventors on Apr. 16, 1974.

More recently, however, manufacturers of air fresheners have again attempted to accomplish the desired results by providing some type of container with a liquid de-odorizer or other air freshener from which extends a wick which may extend to contact some type of head defuser.

Although at least since the device of applicant's aforesaid prior patent, efforts have been made to render room air fresheners decorative—either in the form of flower displays or, more recently, simulating cut crystal jars, one problem with decorative air fresheners has been the inability to make them appear sufficiently aesthetically pleasing so that the housewife would be willing to dispose the item in a living room, dining room, or salon, while making them sufficiently inexpensive to persuade the housewife to buy it. If the air freshener is too expensive, because most of them have not been renewable, the average housewife is reluctant to spend more than a few dollars to purchase one which may have to be discarded after a relatively short period of effective use. On the other hand, if it is made to look cheap, the housewife is reluctant to set it in any room which may contain fine items of art and/or antiques, or other indicia of "class".

There is a great need, therefore, for an air freshener which may have the appearance of a quality item and yet be able to be sold at an acceptable price. It is also desirable that the air freshener have an extensive life so that at least the major portion of it may be retained and still remain effective in accomplishing its intended purpose. This, then, requires that the effective air freshening source be conveniently and inexpensively renewable.

These and other objects are accomplished by the present invention.

SUMMARY OF THE INVENTION

In the preferred embodiment, the present invention provides what appears to be an attractive crystal vase supporting a plurality of attractive flowers projecting above a leaf display. The vase may be comprised of an outer housing which is open at the bottom and the top. The top may be closed by an attractive cap which supportingly holds the stems for artificial flowers and the leaves, but through which cap project one or more stem appearing wicks which extend between one or more vapor dispensers and a source of a volatile air freshening fluid. The outer housing encompasses a fluid-containing vessel fitting therein. The vapor dispensers in one form may be flat head-like elements shaped and colored to simulate artificial leaves; or they may be sponge-like elements formed and colored to appear as an artificial flower or portion thereof. Desirably, each of these vapor dissipating elements is orificed to receive an end of a stem-like wick which is pushed into such orifice and brings the fluid up from the fluid containing vessel.

Within the outer housing is disposed the fluid-containing vessel which may or may not be supported by the cap. This fluid containing vessel itself could be provided with a cap to support a dispensing flower and leaf arrangement in lieu of the housing cap previously described. The vessel is desirably configured to fit matingly within the housing, and is filled with a quantity of the fluid and, before insertion within the housing, is provided with a removable closure to prevent escape of the fluid or gas.

When the dispenser is set up for use, the closure on the fluid container is first removed, the housing may be placed over the container, and one or more wick type stems terminating in a dispensing leaf or flower are inserted into the container and placed in contact with the fluid which it contains. These stems may pass through, and be supported by, either a housing cap, or a cap on the container.

After such period as is required for the fluid in the container to be drawn up through the wick and evaporated through the dispensing leaves and/or flowers, the container may be replaced by simply lifting up the housing with the flower and leaf stems, bringing in a new container, removing its closure and reinserting the stems into the new container as the housing is dropped back over the top of the container. Thereby, the dispenser may be maintained continuously in a state where it is dispensing the air freshening or odorizing fluid.

It is also a feature of the present invention to provide a container with a plurality of sections each containing a fluid with a different aroma so that as the stems are inserted into the different sections, the aroma dispensed may be changed from section to section or mixed.

In addition, sleeve-like covers may be provided for the dispensing pads which covers, when slipped over the dispensing pads, restrict the amount of evaporation of the fluid which reaches the pads through the respective wicks which are inserted into the pads. When removed, the covers then permit full dissipation of the volatile fluid from the pads.

There are, thus, numerous desirable features of the present invention.

BRIEF DESCRIPTION OF THE DRAWINGS

In the accompanying drawings, FIG. 1 is a side elevation showing the invention with its several parts assembled.

FIG. 2 is an elevation of a fluid-containing vessel.

FIG. 3 is a section of a vessel as shown in FIG. 2, but divided vertically into two compartments.

FIG. 4 is a section of a slightly modified form of the housing and vessel portion shown in FIG. 1.

FIG. 5 is a section of the housing and vessel of the embodiment shown in FIG. 1.

FIG. 6 is a section of a still further variation of the housing and vessel of the present invention.

FIG. 7 is an enlarged sectional view taken on the line 7—7 of FIG. 1.

DESCRIPTION OF THE PREFERRED EMBODIMENT

Figure 9:
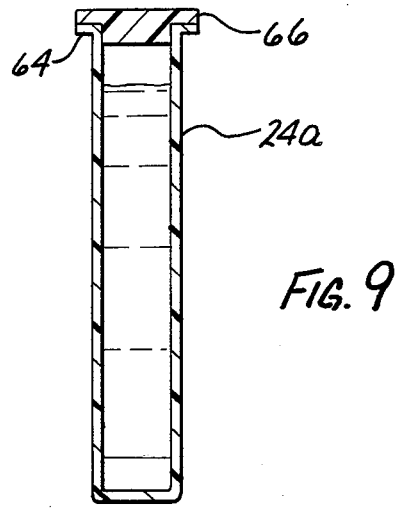
FIG. 9 is an elevation partly in section of the fluid vessel of FIG. 8 from which its plug has been removed.

The present invention may take several forms. Essentially, the end result should appear as a cut glass vase 10 having a cap 12 through which wick-like stems 14 and 16 extend, the former into a simulated leaf pad 18 and the latter into a sponge-like core 20 of an artificial flower 22.

Within the housing 10 is disposed a fluid-containing vessel 24, in one of the several embodiments illustrated in FIGS. 4, 5 and 6. This vessel 24, before it is covered by the housing 10, may come as a separate item filled with fluid 26 and securely closed at its upper end by a cap 28. The vessel 24 may define a single compartment 29 as shown in FIG. 2, or it may be divided internally by at least one vertical wall 30 to provide a plurality of compartments 32, 34, thereby to enable the vessel to be filled with different fluids, the aromas of which, when mixed, may produce an aroma differing from that of each of the fluids in the two to their respective dissipating elements 18 and 20, may be prolonged. This prolongation would be accomplished by removing the temporary plug (not shown) from the second compartment and shifting the stems 14 and 16 into the second compartment after the fluid has been exhausted from the first one.

FIGS. 4, 5 and 6 illustrate several ways in which the fluid containing vessel 24 may be disposed within the outer housing 10. In each of these embodiments, the housing 10 is open both in its top area 36, as well as at its base 38. Thereby, the decorative outer housing 10 may be dropped down over the fluid-containing vessel 24. In the embodiments of FIGS. 4 and 6, both the bottom 40 of the fluid-containing vessel 24, as well as the bottom 38 of the outer housing 10, will rest on the table or other flat surface 42 on which the assembled item is to be disposed. In this FIG. 4 embodiment, as well as that shown in FIG. 6, a cap 44 or 44' respectively, may be provided with orifice 45 to support the wick-like stems 14 and 16. However, in the embodiment of FIG. 5, the cap 44" may be designed with threading to enable it to be screwed into the top 46 of the fluid-containing vessel 24. Thereby the cap 44" will not only support the stems 14 and 16, but it also supports the fluid-containing vessel 24 itself above the horizontal surface 42, by seating on the upper edge 50 of the outer housing 10'

The vessel 24 may be filled with any one of a number of different commerically available aromatic fluids. By inserting a stem-like wick 14 into the vessel in the manner illustrated of FIGS. 4, 5 or 6, fluid will be drawn up the wick which, as illustrated in FIG. 7, terminates in an orifice 51 in the pad-like leaf member 18. Thereby, fluid drawn up the stem-like wick 14 will be passed further into the pad-like element 18 for dissipation into the atmosphere through such element. Similarly, but not shown, the end of the stem-like wick 16 may be inserted into the sponge-like core 20 of the simulated flower 22.

Figure 8:
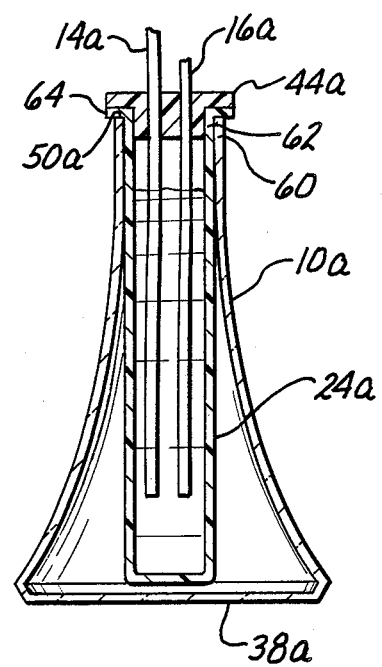
FIG. 8 is an elevation partly in section of a further embodiment.

In the embodiments of FIGS. 4, 5 and 6, the outer housing 10 is open at both its top and its bottom, However, in case there is any concern on the part of the housewife that fluid in the vessel 24 may leak down around its outside and drip into the surface 42, the embodiment of FIG. 8 avoids that possibility by providing a closed bottom 38a for the housing. However, since the housing 10a cannot be dropped down over the vessel 24a, but the latter must be passed through the neck 60 of the housing 10a, the outside diameter of the vessel 24a must, at no point below its upper rim 62, be as great as the inside diameter of the neck 60 of the housing 10a. Desirably, for easy removal the upper rim 62 of the vessel 24a should be flanged at 64. Thereby, the vessel 24a may be supported on the upper rim 50a of the housing 10a.

In this FIG. 8 embodiment, the vessel 24a may be sold as a separate unit in the form shown in FIG. 9, in which case, it is initially closed at the top by a cap 66. When the assembly is to be set up to function as a deodorizer, the cap 66 on the vessel 24a is removed and the latter is lowered through the neck 60 until the vessel flange 64 seats on the housing rim 50a. At this point, the leaf and flower stem bearing cap 44a is inserted inside the vessel 24a so that the wick-like stems 14a, 16a extend down into the fluid 26a and the assembly then functions in the same manner as the embodiments of FIGS. 4, 5 and 6 hereinabove described. It should be pointed out, however, that when the FIG. 8 embodiment is to be marketed, the vessel 24a should not be inserted in the housing 10a unless it is desired to demonstrate its olfactory effect. Instead, only the leaf and flower bearing cap 44a would be mounted on the rim 50a, to be removed later when the veseel 24a is inserted for activation of the assembly, and set up in the manner hereinabove described.

It is also a feature of the present invention to provide a thin impervious jacket 52 which may be slipped over the leaf-like pad 18 (FIG. 7) when it is desired to minimize the dissipation of the air cleansing or odorizing gas from the element 18. A similar covering (not illustrated) could be provided for the sponge-like core 20 of the flower 22, but because of its shape, the flower 22 does not lend itself as well to such covering as the leaf-like pad 18.

The stem-like wick 14 desirably is constructed of a flexible wire core 54 about which is wound an absorbent material commonly used for lamp wicks.

In use, then, depending upon whether the FIGS. 4 and 6 embodiment or the FIG. 5 embodiment is employed, the cap 28 is first removed from the fluid-containing vessel 24 and the latter is brought into co-axial alignment with the outer housing 10 which is then dropped down over the vessel 24. In the case of the FIG. 4 embodiment, the flower or flowers 22 and leaf-like element 18 and their respective stems 16 and 14 are inserted through the cap 44 and then moved downwardly to where the lower ends 14a and 16a of the wicks 14 and 16 respectively, are inserted as far down into the fluid filled vessel 14 as possible. The cap 44 which is then be either set on the upper edge 50 of the outer housing 10, and the stem-like wicks 14 and 16 are then bent to arrange the flowers 22 and the leaf-like elements 18 in a manner most closely resembling a vase filled with live flowers and leaves.

Whenever the fluid 26 in the vessel 24 becomes exhausted, it is a simple matter to replace the vessel by simply lifting up the outer housing 10 with the cap 44 and stems 14 and 16 protruding below it, uncapping a new vessel 24 and placing under the housing 10 and unseating the wicklike stems, in the manner first described.

In the embodiment of FIG. 5, the assembly differs only in that the cap 44' is screwed into the threaded area 46 at the top of the vessel 24 after the vessel is first brought in under the housing and co-axially aligned with the neck area of the latter. The stems 14 and 16 desirably are inserted through the cap 44' before it is screwed into the threading 46.

If it is desired to utilize the form of the liquid containing vessel of FIG. 3, the orifice 45 in the cap 44, must be sufficient to enable the number of wick-like stems 14, 16 to be inserted in one or more of the compartments 32, 34.

Although In FIG. 1, only one flower and one leaf-like element is shown, it can be understood that multiple leaves and/or flowers, whether or not in the form of the element 18 and the flower 22, may be made to protrude from the cap 44, 4' or 44" to improve the appearance of the display. Of course, if no dissipating element such as 18 or 20 is incorporated in any leaf flower, there is no need for the stems of such leaves or flowers to extend any distance below the respective cap 44, 44' or 44", if at all. Actually, the non-functional artificial flower and leaves could be permanently molded into any of such caps.

It may, thus, be seen that the present invention provides for a decorative air freshener in the form of not only a decorative vase with type flower display, but one in which both the display and the outer housing may be kept for as long as the housewife may desire. At any time the fluid in the vessel 24 becomes exhausted through the capillary action of the stem-like wicks 14 and 16, which carry the fluid to the elements 18 and 20, the inner vessel may easily be replaced. In this way, it is not necesary for the housewife to discard the major portion of the air freshener or odorizer. In addition, through the use of the jacket 52, she may attenuate, to some extent, the rate at which the fluid is drawn into the element 18 (and/or 20), thereby extending the life of the fluid-containing vessel 24.

The present invention, thus, may be seen to provide very useful functions which have not heretofore been accomplished by devices of the prior art.

We claim:

1. An artificial horticultural product air freshener combination comprising:
   (a) a first outer vessel, said first vessel being in the form of a vase having a base portion from which upwardly and inwardly tapers a neck portion which neck portion defines an open passageway, said passageway having a predetermined diameter and open at its upper extremity;
   (b) a second inner vessel, said second vessel being closed at its bottom and having a lower portion and an upper portion, said second vessel being disposable within the first vessel and having an outer diameter for its upper portion which is less than said predetermined diameter of the passageway defined by the neck portion of said first vessel, said second vessel containing a volatile fluid, the vapor of which, when allowed to dissipate into the atmosphere, produces a desired olfactory effect, said second vessel having an opening at the top of its upper portion and a removable first closure for said opening;
   (c) a second orificed closure to replace the first closure upon its removal;
   (d) a decorative artificial horticultural product, said product including a sponge-like element, said element having an opening into its interior; and
   (e) an elongated wick, said wick being in a form simulating a plant or leaf stem, one end of said wick being removably insertable in said opening in said element and the other end of said wick being passed through the orifice in the second closure to extend down through the said opening in the second vessel and into contact with the fluid container therein.

2. The combination as described in claim 1 wherein said stem-like wick provides support for the element into the opening of which it is inserted.

3. The combination as described in claim 1 in which a removable and replaceable impervious jacket is provided substantially to encompass at least one of said sponge-like elements, thereby to restrict the rate of dissipation of such of said fluid as is drawn up through the wick to said element.

4. The combination as described in claim 1 wherein the horticultural product comprises at least one artificial flower and said sponge-like element is flat and in the form of a plant leaf and both said flower and said element are provided with flexible stems passed through the orifices in said second closure and extending down to and supported with reference to the second vessel.

5. The combination as described in claim 1 wherein the second vessel is divided by a vertical wall into two separate compartments each containing a volatile fluid which, when evaporated, produces a different olfactory effect from that produced by the other fluid, and at least two separately supported sponge-like elements are provided, each being supported by a flexible stem-like wick passed through an orifice in the second closure to extend downwardly into a different compartment in contact with the fluid in such compartment, said fluids being of such nature that, when their vapors are simultaneously dissipated in the same area, a different olfactory effect is produced from that produced by either of said fluids alone.

6. An artificial horticultural product air freshener combination comprising:
   (a) a first outer vessel, said first vessel being in the form of a vase having a base portion from which upwardly and inwardly tapers a neck portion which neck portion defines an open passageway, said passageway having a predetermined diameter and open at its upper extremity,
   (b) a second inner vessel, said second vessel being closed at its bottom and having a lower portion and an upper portion, said second vessel being disposable within the first vessel and having an outer diameter for its upper portion which is less than said predetermined diameter of the passageway defined by the neck portion of said first vessel, said second vessel containing a volatile fluid, the vapor of which, when allowed to dissipate into the atmosphere, produces a desired olfactory effect, said vessel having an opening at the top of its upper portion and a removable first closure for said opening;

(c) a second orificed closure to replace the first closure upon its removal; and (d) an artificial horticultural product arrangement, said arrangement including at least one artificial flower and at least one artificial leaf, said flower being supported with reference to said second vessel by a first downwardly extending elongated flexible stem and said leaf being formed of a flat sponge-like pad having an opening therein, said leaf being supported with reference to said second vessel by a second elongated flexible stem passed through an orifice in said second closure and into the said second vessel to extend downwardly with said first stem into said second vessel, at least one of said stems being in the form of a wick which extends into the second vessel to contact the fluid, thereby to conduct by capillary action the fluid from the second vessel up to the flower or leaf which it supports.

7. The combination as provided in claim 6 wherein the orifices closure for the second vessel extends radially to an extent at least as great as the outer diameter of the upper terminus of the neck of the first vessel and includes a cylindrical shell portion extending downwardly to fit tightly within the top of the second vessel, whereby the second vessel may be supported within the first vessel and above its closed bottom by the second orificed closure resting on the top of the neck of the first vessel.

8. The combination as described in claim 6 wherein the first outer vessel is formed to appear as cut crystal.

9. The combination as described in claim 6 wherein the at least one wick is removably inserted in the opening in the flat sponge-like pad forming a leaf.

10. The combination as described in claim 6 wherein the base of the outer vessel is decorative and is open at its bottom.

11. The combination as described in claim 10 wherein the stem-like wicks are permanently secured within the orificed second closure so that the horticultural product arrangement may be removed from the second vessel to facilitate the replacement of the second vessel with a new second vessel in the combination when the fluid in the second vessel has been exhausted.

12. The combination as described in claim 6 wherein the first vessel has a closed bottom and the second vessel is of such configuration as to be insertable through the passageway defined by the neck of the first vessel and is supported on the upper terminus of said neck.

* * * * *